United States Patent
Dawoud et al.

(10) Patent No.: US 11,058,344 B2
(45) Date of Patent: Jul. 13, 2021

(54) METHOD AND SYSTEM TO ACCELERATE CONFIRMATION OF CARDIAC ARRHYTHMIAS

(71) Applicant: Pacesetter, Inc., Sylmar, CA (US)

(72) Inventors: Fady Dawoud, Santa Monica, CA (US); Diming Cao, Valley Village, CA (US)

(73) Assignee: PACESETTER, INC., Sylmar, CA (US)

( * ) Notice: Subject to any disclaimer, the term of this patent is extended or adjusted under 35 U.S.C. 154(b) by 363 days.

(21) Appl. No.: 16/382,095

(22) Filed: Apr. 11, 2019

(65) Prior Publication Data

US 2020/0323458 A1  Oct. 15, 2020

(51) Int. Cl.
*A61B 5/0464* (2006.01)
*A61B 5/363* (2021.01)
(Continued)

(52) U.S. Cl.
CPC .............. *A61B 5/363* (2021.01); *A61B 5/352* (2021.01); *A61B 5/364* (2021.01); *A61B 5/366* (2021.01);
(Continued)

(58) Field of Classification Search
CPC ....... A61B 5/352; A61B 5/3622; A61B 5/363; A61B 5/364; A61B 5/366; A61B 5/361;
(Continued)

(56) References Cited

U.S. PATENT DOCUMENTS

| 2013/0053714 | A1 | 2/2013 | Bornzin et al. |
| 2014/0276160 | A1 | 9/2014 | Zhang et al. |
| 2014/0288451 | A1 | 9/2014 | Brodnick et al. |

OTHER PUBLICATIONS

Extended European Search Report for corresponding EP Application No. 20166859.7-1115 dated Apr. 9, 2020.

*Primary Examiner* — Alyssa M Alter
(74) *Attorney, Agent, or Firm* — The Small Patent Law Group LLC; Dean D. Small

(57) ABSTRACT

A system and method for accelerating confirmation of cardiac arrhythmias is provided. The system includes memory to store specific executable instructions. One or more processors are configured to execute the specific executable instructions for obtaining a far field cardiac activity (CA) data set that includes far field CA signals for a series of beats. The CA data set includes a first CA data subset and a remainder CA data subset. The system analyzes the CA data set for an arrhythmia of interest utilizing a primary detection process having primary criteria. During a first phase of the primary detection process the system analyzes the first CA data subset to determine whether the first CA data subset satisfies at least a portion of the primary criteria. When the first CA data subset satisfies at least the portion of the primary criteria, the system initiates a secondary confirmation process. Parallel and contemporaneous in time the system i) analyzes the first CA data subset utilizing secondary criteria associated with the secondary confirmation process and ii) analyzes the remainder CA data subset utilizing the primary criteria. The system declares the CA data set to exhibit an arrhythmia episode when the first CA data subset satisfies the secondary criteria and the remainder CA data subset satisfies a remainder of the primary criteria.

20 Claims, 11 Drawing Sheets

(51) Int. Cl.
*A61B 5/00* (2006.01)
*A61N 1/362* (2006.01)
*A61B 5/352* (2021.01)
*A61B 5/364* (2021.01)
*A61B 5/366* (2021.01)
A61B 18/00 (2006.01)
A61N 1/04 (2006.01)
A61N 1/05 (2006.01)
A61N 1/39 (2006.01)
A61B 5/316 (2021.01)
A61B 5/361 (2021.01)

(52) U.S. Cl.
CPC .......... *A61B 5/7221* (2013.01); *A61N 1/3622* (2013.01); *A61B 5/0006* (2013.01); *A61B 5/316* (2021.01); *A61B 5/361* (2021.01); *A61B 5/4836* (2013.01); *A61B 5/686* (2013.01); *A61B 5/7203* (2013.01); *A61B 2018/00392* (2013.01); *A61N 1/046* (2013.01); *A61N 1/0587* (2013.01); *A61N 1/3968* (2013.01)

(58) Field of Classification Search
CPC .......... A61B 5/316; A61B 2018/00392; A61B 5/4836; A61B 5/686; A61N 1/0578; A61N 1/3968; A61N 1/046
See application file for complete search history.

METHOD AND SYSTEM TO ACCELERATE CONFIRMATION OF CARDIAC ARRHYTHMIAS

FIELD OF THE INVENTION

Embodiments herein relate generally to implantable medical devices, and more particularly to accelerated detection and discrimination of arrhythmic patterns of interest.

BACKGROUND OF THE INVENTION

Cardiac monitoring systems have been developed for use in an ambulatory setting, which may be either external, such as a Holter monitor, or internal, such as implantable cardiac monitors or "loop recorders". These systems continually sense cardiac electrical signals from a patient's heart, process the signals to detect arrhythmias and upon detection, record the electrical signals for subsequent review and analysis.

More recently, interest has increased in providing improved the implantable cardiac monitor (ICM). It has been proposed that implantable cardiac monitors may be used for collecting electrocardiogram (ECG) signals and diagnosis of various arrhythmias, including tachycardia, Bradycardia, asystole and the like.

Undersensing is a wide-spread challenge inherent in sensing ECG signals by remote cardiac measurements (non-vascular e.g., subcutaneous or substernal) due to loss of device-skin contact, posture change or other means. Even though clinic programming during implantation tries to optimize parameters, an ECG R-wave amplitude changes over time (mostly decreases) leading to false triggers due to undersensing of the ECG signal.

An approach, that is employed in ICMs to mitigate undersensing, is to use a secondary confirmation algorithm. The secondary confirmation algorithm uses a measured or filtered ECG signal after a tachycardia, Bradycardia or asystole episode is declared. FIG. 1A illustrates a current flow of ICM primary detection and secondary confirmation processing. When a primary detection process determines that all criteria are satisfied for Bradycardia, tachycardia or an asystole arrhythmia, a secondary confirmation process is initiated.

FIG. 1B illustrates a conventional ECG strip and episode marker. As shown in FIG. 1B, once the primary detection process completes the analysis and declares a potential episode, a period of time (e.g., 1 second) passes before the secondary confirmation process completes analysis. The secondary confirmation process uses a more sensitive threshold to further verify the presence of arrhythmic beats. The ICM holds the outcome of the primary detection process as a potential episode until the secondary confirmation process analyzes a segment of ECG data. The ICM does not label the potential episode with an episode marker (e.g., "Brady") until the secondary confirmation process confirms the episode.

Hence, a noticeable processing delay occurs from the completion of the primary detection process, while the secondary confirmation process analyzes the ECG data, until the secondary confirmation generates an outcome confirming or rejecting the candidate episode. An ECG strip and marker are displayed. However, the delay introduces a visible offset on the display between a location where an episode marker is inserted onto an ECG signal and the actual point along the ECG signal where the arrhythmia episode occurred. In the example of FIG. 1B, the actual Brady episode should be labeled with a marker at the 10 second "10 s" time point along the ECG strip, but instead the "Brady" marker is inserted after the $11^{th}$ second "11 s" along the ECG strip. The Bradycardia marker is positioned along the ECG strip over 1 second after the actual point at which the Bradycardia episode was declared.

Further, the secondary confirmation algorithm uses logic operations to either confirm or reject a potential episode in addition to the primary detection operation. After the primary detection process declares a potential episode, the secondary confirmation logic then begins to process the available data, before the ICM generates and records an episode marker with the ECG signals. Depending on the ICM setting, the secondary confirmation process can delay generation (e.g., by 1 or more seconds) of the episode marker on a display of a programmer or on a patient care network report. The time needed for the secondary confirmation algorithm to confirm or deny an episode can also inhibit or delay execution of discriminators leading to user confusion.

Also, a common reason for declaration of false episodes is that the primary detection process experiences persistent undersensing for an extended duration of time. Persistent undersensing causes the ICM to utilize undue processor power to appropriately handle the undersensed events (both by primary detection and secondary confirmation processes) which can translate to shortened device longevity from days to months. Further, undersensing can lead to undue use of storage space to store inappropriate arrhythmia episodes as well as Bluetooth time to transmit stored episodes to an external instrument.

An opportunity remains to accelerate the process for confirming or rejecting arrhythmia episodes as well as to better align in time recorded and displayed episode markers and cardiac activity signals on a display and report.

SUMMARY

In accordance with embodiments herein, a system for accelerating confirmation of cardiac arrhythmias is provided. The system includes memory to store specific executable instructions. One or more processors are configured to execute the specific executable instructions for obtaining a far field cardiac activity (CA) data set that includes far field CA signals for a series of beats. The CA data set includes a first CA data subset and a remainder CA data subset. The system analyzes the CA data set for an arrhythmia of interest utilizing a primary detection process having primary criteria. During a first phase of the primary detection process the system analyzes the first CA data subset to determine whether the first CA data subset satisfies at least a portion of the primary criteria. When the first CA data subset satisfies at least the portion of the primary criteria, the system initiates a secondary confirmation process. Parallel and contemporaneous in time the system i) analyzes the first CA data subset utilizing secondary criteria associated with the secondary confirmation process and ii) analyzes the remainder CA data subset utilizing the primary criteria. The system declares the CA data set to exhibit an arrhythmia episode when the first CA data subset satisfies the secondary criteria and the remainder CA data subset satisfies a remainder of the primary criteria.

Optionally, the one or more processors may be configured to complete the analysis of the first CA data set by the secondary confirmation process before or substantially contemporaneous in time with completion of the analysis of the remainder of the CA data subset by the primary detection process. The one or more processors may be further configured to reject the arrhythmia episode when at least one of the i) analysis determines that the first CA data subset does not satisfy the secondary criteria or the ii) analysis determines that the remainder CA data subset does not satisfy the primary criteria. The primary detection process may detect Bradycardia episodes. The one or more processors may be configured to initiate the secondary confirmation process in response to the first CA data subset including a first number of Bradycardia beats. The one or more processors may be configured to implement the ii) analysis by determining that the remainder CA data subset satisfies the remainder of the primary criteria when the remainder CA data subset includes a second number of Bradycardia beats.

Optionally, the at least the portion of the primary criteria may include an initial criteria to be applied to the first CA data subset and a remainder of the primary criteria to be applied to the remainder CA data subset. The primary detection process may detect asystole episodes. The one or more processors may be configured to initiate the secondary confirmation process in response to the first CA data subset including a first time interval during which no R waves are detected by the primary detection process. The one or more processors may be configured to declare a candidate asystole episode when the ii) analysis determines that the primary detection process does not detect an R-wave during the remainder CA data subset. The primary detection process may detect Bradycardia episodes. The one or more processors may be configured to initiate the secondary confirmation process in response to the primary detection process determining that the first CA data subset exhibits a number of Bradycardia events. The one or more processors may be configured to declare a candidate Bradycardia episode when the ii) analysis determines that the primary detection process detects at least one Bradycardia event during the remainder CA data subset.

Optionally, the one or more processors may be further configured to record a Brady or asystole marker with the CA data set at a point along the CA data set that substantially corresponds in time to a culmination point along the CA dataset of a corresponding Brady or asystole episode. The one or more processors may be further configured to maintain a count of candidate arrhythmia episodes that are rejected based on the secondary confirmation process; and to adjust a sensitivity profile parameter of the primary detection process based on the count. The one or more processors may be further configured to revert to a programmed sensitivity profile of the primary detection process after expiration of a timer.

In accordance with embodiments herein, a computer implemented method for accelerating confirmation of cardiac arrhythmias is provided. The method is under control of one or more processors configured with specific executable instructions. The method obtains a far field cardiac activity (CA) data set that includes far field CA signals for a series of beats. The CA data set includes a first CA data subset and a remainder CA data subset. The method analyzes the CA data set for an arrhythmia of interest utilizing a primary detection process having primary criteria. During a first phase of the primary detection process the method analyzes the first CA data subset to determine whether the first CA data subset satisfies at least a portion of the primary criteria. When the first CA data subset satisfies at least the portion of the primary criteria, the method initiates a secondary confirmation process. Parallel and contemporaneous in time the method i) analyzing the first CA data subset utilizing secondary criteria associated with the secondary confirmation process and ii) analyzing the remainder CA data subset utilizing the primary criteria. The method declares the CA data set to exhibit an arrhythmia episode when the first CA data subset satisfies the secondary criteria and the remainder CA data subset satisfies a remainder of the primary criteria.

Optionally, the method may comprise completing the i) analysis of the first CA data set by the secondary confirmation process before or substantially contemporaneous in time with completion of the analysis of the remainder of the CA data subset by the primary detection process. The method may reject the arrhythmia episode when at least one of the i) analysis determines that the first CA data subset does not satisfy the secondary criteria or the ii) analysis determines that the remainder CA data subset does not satisfy the primary criteria. The primary detection process may detect Bradycardia episodes. The method may initiate the secondary confirmation process in response to the first CA data subset including a first number of Bradycardia beats. The method may implement the ii) analysis by determining that the remainder CA data subset satisfies the remainder of the primary criteria when the remainder CA data subset includes a second number of Bradycardia beats.

Optionally, the at least the portion of the primary criteria may include an initial criteria to be applied to the first CA data subset and a remainder of the primary criteria to be applied to the remainder CA data subset. The primary detection process may detect asystole episodes. The method may initiate the secondary confirmation process in response to the first CA data subset including a first time interval during which no R waves are detected by the primary detection process. The method may declare a candidate asystole episode when the ii) analysis determines that the primary detection process does not detect an R-wave during the remainder CA data subset.

Optionally, the primary detection process may detect Bradycardia episodes. The method may initiate the secondary confirmation process in response to the primary detection process determining that the first CA data subset exhibits a select number of Bradycardia events. The method may declare a candidate Bradycardia episode when the ii) analysis determines that the primary detection process detects at least one Bradycardia event during the remainder CA data subset. The method may record a Brady or asystole marker with the CA data set at a point along the CA data set that substantially corresponds in time to a culmination point of a corresponding Brady or asystole episode.

Optionally, the method may maintain a count of candidate arrhythmia episodes that are rejected based on the secondary confirmation process; and adjusting a sensitivity profile parameter based on the count. The method may utilize a beat to beat stability criteria to test for proper R wave sensing, and based thereon adjusting a sensitivity profile parameter, the beat-to-beat variability metrics including one or more of an RR interval, R wave amplitude, or R wave area-under-the-curve.

TERMS AND ABBREVIATIONS

Figure 1A:
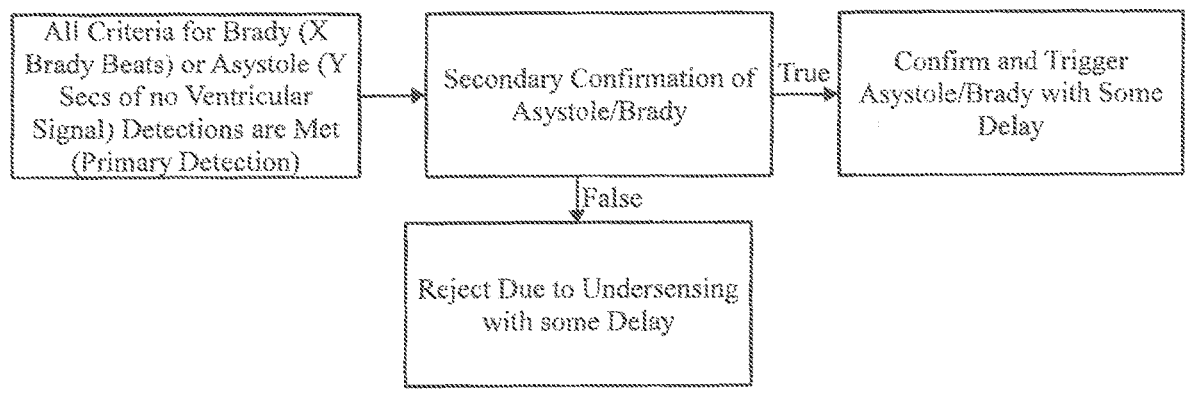
FIG. 1A illustrates a current flow of ICM primary detection and secondary confirmation processing in accordance with embodiments herein.
Figure 1B:
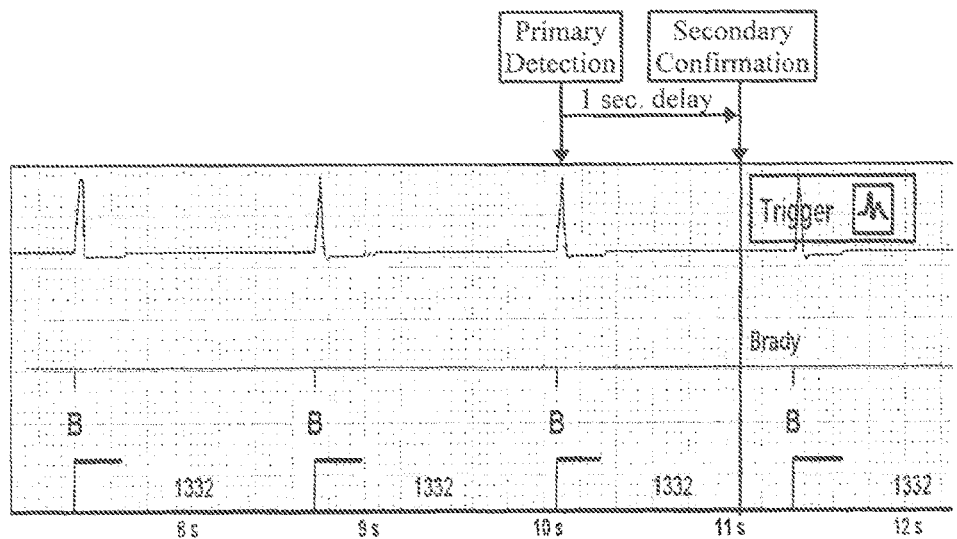
FIG. 1B illustrates a conventional ECG strip and episode marker in accordance with embodiments herein.

The terms "cardiac activity signal". "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/ arrhythmic. Non-limiting examples of CA signals include ECG signals collected by cutaneous electrodes, and EGM signals collected by subcutaneous electrodes.

The terms "cardiac activity data set" and "CA data set" (collectively "CA data set") are used interchangeably to refer to a data set that includes measured CA signals for a series of cardiac events in combination with device documented markers.

The term "CA data subset" refers to a portion (but not all) of a CA data set.

The term "marker" refers to data and/or information identified from CA signals that may be presented as graphical and/or numeric indicia indicative of one or more features within the CA signals and/or indicative of one or more episodes exhibited by the cardiac events. Markers may be superimposed upon CA signals or presented proximate to, and temporally aligned with, CA signals. Non-limiting examples of markers may include R-wave markers, noise markers, activity markers, interval markers, refractory markers, P-wave markers, T-wave markers, PVC markers, sinus rhythm markers, AF markers and other arrhythmia markers. As a further non-limiting example, basic event markers may include "AF entry" to indicate a beginning of an AF event, "in AF" to indicate that AF is ongoing, "AF exit" to indicate that AF has terminated, "T" to indicate a tachycardia beat, "B" to indicate a Bradycardia beat, "A" to indicate an asystole beat, "VS" to indicate a regular sinus beat, "Tachy" to indicate a tachycardia episode, "Brady" to indicate a Bradycardia episode, "Asystole" to indicate an asystole episode, "Patient activated" to indicate a patient activated episode. An activity marker may indicate activity detected by activity sensor during the CA signal. Noise markers may indicate entry/start, ongoing, recovery and exit/stop of noise. Markers may be presented as symbols, dashed lines, numeric values, thickened portions of a waveform, and the like. Markers may represent events, intervals, refractory periods, ICM activity, and other algorithm related activity. For example, interval markers, such as the R-R interval, may include a numeric value indicating the duration of the interval. The AF markers indicate atrial fibrillation rhythmic.

The term "COI" refers to a characteristic of interest within CA signals. Non-limiting examples of features of interest include an R-wave, P-wave, T-wave and isoelectric segments. A feature of interest may correspond to a peak of an individual R-wave, an average or median P, R or T-wave peak and the like.

The terms "culmination Point", "conclusion Point" and "episode designation" are used interchangeably to refer to a point along a CA signal or CA strip at which a final criteria or final factor occurred that satisfies the primary criteria of the primary detection process. For example, the culmination point is a point along an ECG strip where an asystole window ends without an R-wave detected in the asystole window. The culmination point occurs in a Bradycardia episode at the point along the ECG strip where a final Brady beat R-wave is detected.

The terms "beat" and "cardiac event" are used interchangeably and refer to both normal or abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, a un-healthy or abnormal functioning of the heart.

The term "real-time" refers to a time frame contemporaneous with a normal or abnormal episode occurrence. For example, a real-time process or operation would occur during or immediately after (e.g., within minutes or seconds after) a cardiac event, a series of cardiac events, an arrhythmia episode, and the like.

The term "sensitivity", as used herein, refers to a threshold that an input CA signal must exceed for an implantable device to identify a CA signal feature of interest (e.g., an R-wave). As one non-limiting example, software may be implemented using a programmed sensitivity level to declare an R-wave to be detected when the input CA signal exceeds the current programmed sensitivity level In response, the software declares a device documented feature (e.g., R-wave) marker. The sensitivity level may be defined in various manners based on the nature of the CA signals. For example, when the CA signals measure electrical activity in terms of millivolts, the sensitivity level represents a millivolt threshold. For example, when a cardiac beat with a 0.14 mV amplitude is sensed by a device hardware, and R-wave may be detected when the current sensitivity level is programmed to 0.1 mV. However, when the sensitivity level is programmed to 0.15 mV or above, a cardiac beat with amplitude of 0.14 mV will not be detected as an R-wave. Embodiments herein determine an adaptive sensitivity limit and sensitivity profile for the sensitivity level.

Overview

Embodiments herein describe novel methods and systems to accelerate validation of a declaration of an arrhythmia episode (e.g., Brady and asystole). To do so, embodiments herein initiate data pre-processing by a secondary confirmation process, when partial conditions of an arrhythmia are met within a primary detection process. The secondary confirmation process is initiated before an arrhythmia is declared by the primary detection process, such that the confirmation process generates an outcome before or at a common time as completion of the primary detection process. By performing the primary detection and secondary confirmation processes in parallel, methods and systems herein generate and position episode markers at a same point in time along a CA signal/strip (e.g., ECG signals) as an actual point along the CA signal where the arrhythmia was identified. By performing the primary detection and secondary confirmation processes in parallel, methods and systems herein are able to store the episode markers and CA signals in the data storage and/or display the markers and ECG signals with minimal offset or time delay therebetween. By performing the primary detection and secondary confirmation processes in parallel, methods and systems herein are able minimize negative impacts on other features, such as postponed execution, or racing condition, etc. Embodiments herein avoid waiting to initiate/execute a secondary confirmation process until after all conditions for the primary detection process are met. Embodiments implement novel methods and systems to expedite the confirmation of the arrhythmia by performing pre-processing when a partial set of conditions, needed to detect an episode, are met. Also, methods and systems herein avoid under-sensing situations altogether, thereby reducing battery usage associated with secondary discriminators computational processing.

Figure 2:
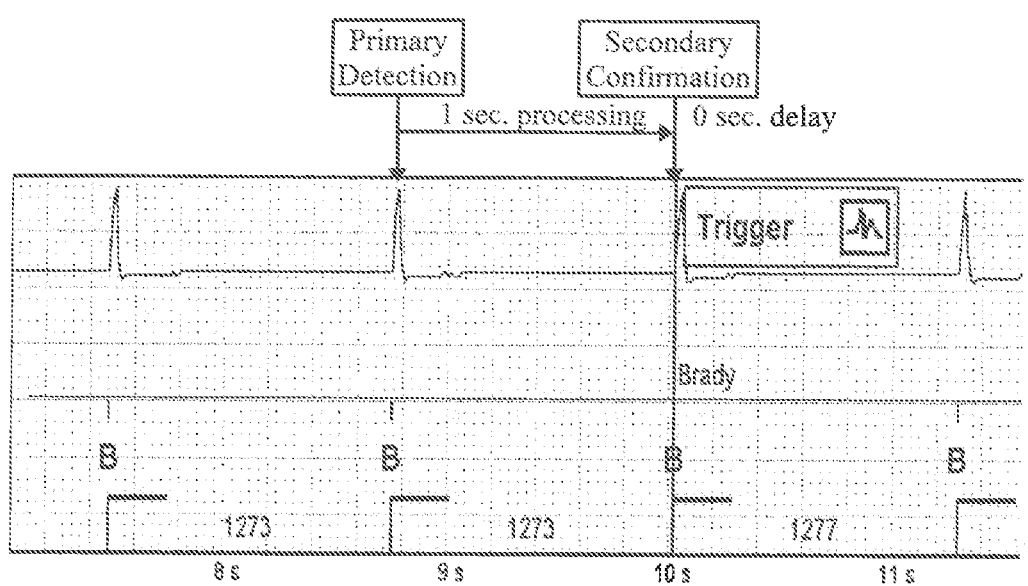
FIG. 2 illustrates an ECG strip and episode markers along with designators for a start time for the secondary confirmation process and a culmination point for the primary detection process in accordance with embodiments herein.

By initiating the secondary confirmation process prior to satisfaction of all detection (or trigger) criteria in the primary detection process (e.g., after 3 out of 4 Bradycardia beats are sensed or after 2.5 out of 3 seconds of asystole timer has elapsed), embodiments herein expedite presentation of arrhythmia markers (as shown in FIG. 2). FIG. 2 illustrates an ECG strip and episode markers along with designators for a start time for the secondary confirmation process and a culmination point for the primary detection process in accordance with embodiments herein.

Optionally, the methods and systems herein adjust sensitivity parameters utilized with the primary detection process in order to improve ICM longevity by avoiding undue battery drain that would otherwise occur with persistent undersensing.

Figure 3:
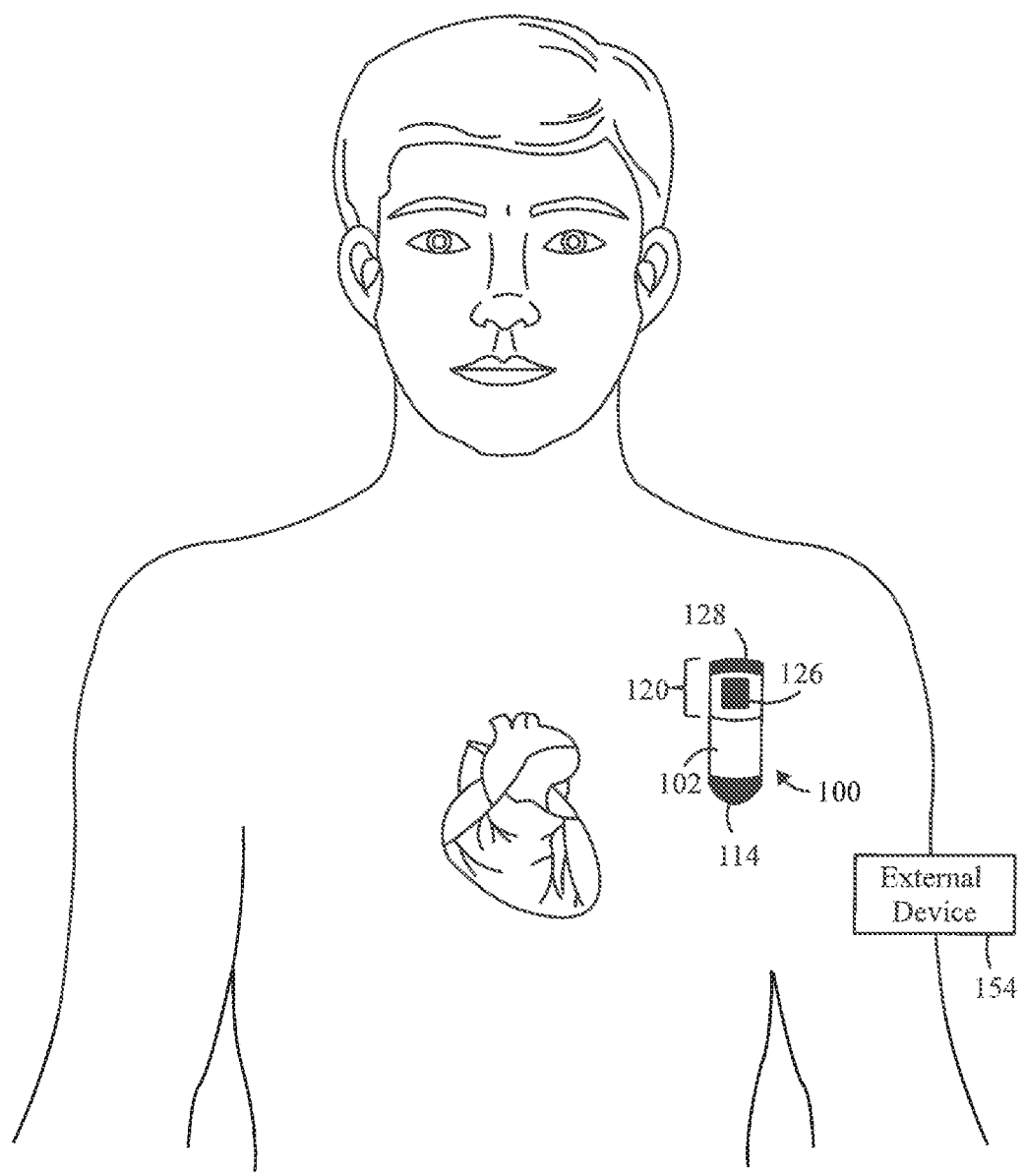
FIG. 3 illustrates an implantable cardiac monitoring device (ICM) intended for subcutaneous implantation at a site near the heart in accordance with embodiments herein.

FIG. 3 illustrates an implantable cardiac monitoring device (ICM) 100 intended for subcutaneous implantation at a site near the heart. The ICM 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the ICM 100, while the electrode 126 is located on a proximal side of the ICM 100. Additionally or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the AF detection algorithm described herein, a loop memory for temporary storage of CA data, a device memory for long-term storage of CA data upon certain triggering events, such as AF detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The ICM 100 may be configured to be activated by the patient or automatically activated, in connection with recording-subcutaneous ECG signals.

The ICM 100 senses far field, subcutaneous CA signals, processes the CA signals to detect arrhythmias and if an arrhythmia is detected, automatically records the CA signals in memory for subsequent transmission to an external device 154. The CA signal processing and AF detection is provided for, at least in part, by algorithms embodied in or implemented by the microprocessor. The ICM 100 includes one or more processors and memory that stores program instructions directing the processors to implement AF detection utilizing an on-board R-R interval irregularity (ORI) process that analyzes cardiac activity signals collected over one or more sensing channels.

Figure 4A:
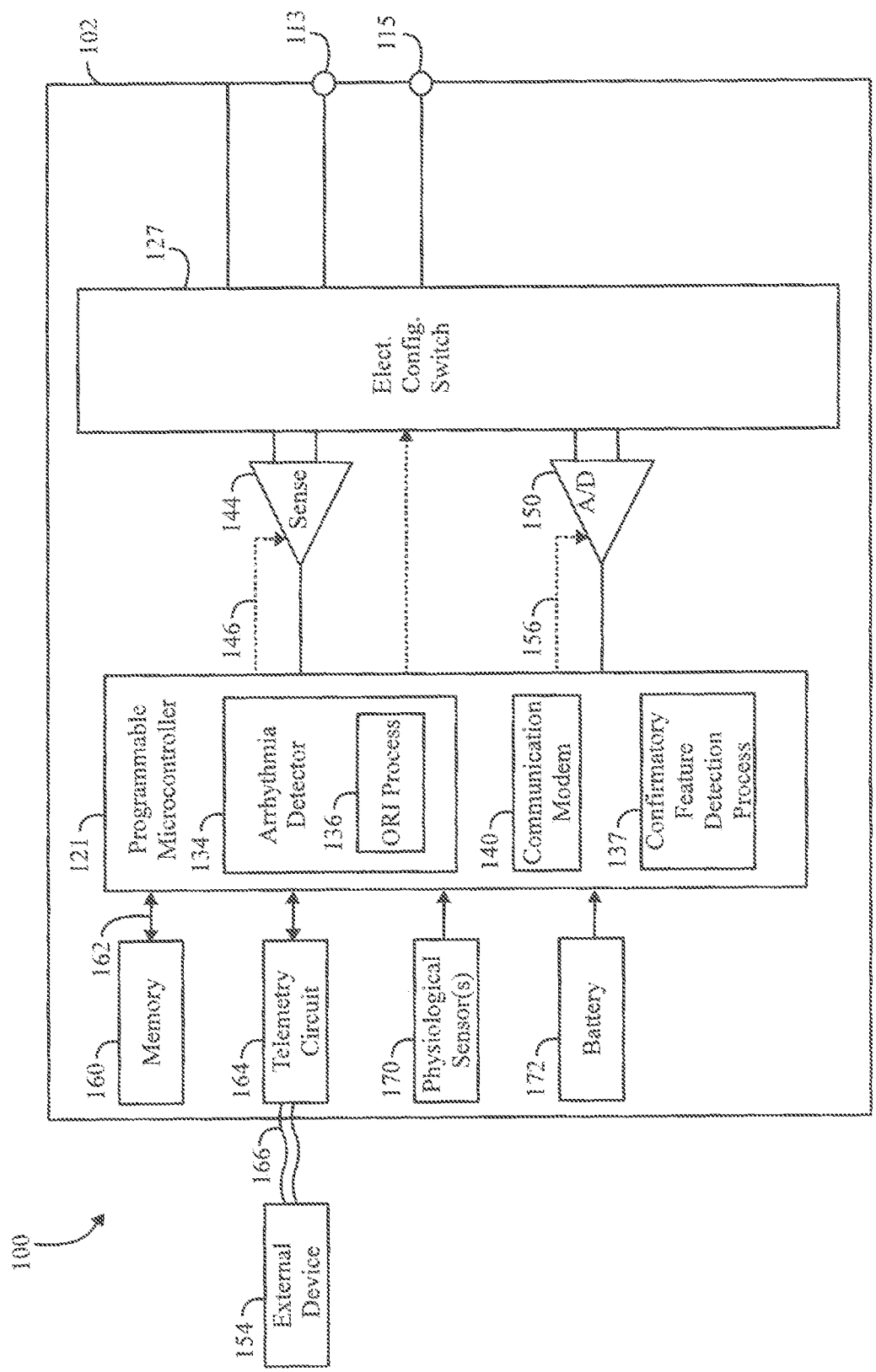
FIG. 4A shows a block diagram of the ICM formed in accordance with embodiments herein.

FIG. 4A shows a block diagram of the ICM 100 formed in accordance with embodiments herein. The ICM 100 may be implemented to monitor ventricular activity alone, or both ventricular and atrial activity through sensing circuitry. The ICM 100 has a housing 102 to hold the electronic/computing components. The housing 102 (which is often referred to as the "can", "case", "encasing", or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with collecting cardiac activity data and analyzing the cardiac activity data.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal from the microcontroller 121. Optionally, the switch 127 may be omitted and the I/O circuits directly connected to the housing electrode 114 and a second electrode 126. Microcontroller 121 includes an arrhythmia detector 134 that is configured to analyze cardiac activity signals to identify potential A arrhythmias (e.g., Tachcardias, Bradycardas, Asystole, etc.). By way of example, the arrhythmia detector 134 may implement an AF detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies.

The ICM 100 is further equipped with a communication modem (modulator/demodulator) 140 to enable wireless communication. In one implementation, the communication modem 140 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuitry 144 selectively coupled to one or more electrodes that perform sensing operations, through the switch 127 to detect cardiac activity. The sensing circuitry 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches.

The output of the sensing circuitry 144 is connected to the microcontroller 121 which, in turn, determines when to store the cardiac activity data of CA signals (digitized by the A/D data acquisition system 150) in the memory 160. For example, the microcontroller 121 may only store the cardiac activity data (from the A/D data acquisition system 150) in the memory 160 when a potential episode is detected. The sensing circuitry 144 receives a control signal 146 from the microcontroller 121 for purposes of controlling the gain, threshold, polarization charge removal circuitry (not shown), and the timing of any blocking circuitry (not shown) coupled to the inputs of the sensing circuitry.

In the example of FIG. 4A, a single sensing circuit 144 is illustrated. Optionally, the ICM 100 may include multiple sensing circuits, similar to sensing circuit 144, where each sensing circuit is coupled to two or more electrodes and controlled by the microcontroller 121 to sense electrical activity detected at the corresponding two or more electrodes. The sensing circuit 144 may operate in a unipolar sensing configuration or in a bipolar sensing configuration. Optionally, the sensing circuit 144 may be removed entirely and the microcontroller 121 perform the operations described herein based upon the CA signals from the A/D data acquisition system 150 directly coupled to the electrodes.

The arrhythmia detector 134 of the microcontroller 121 is configured to perform a primary detection process to detect arrhythmias, such as tachycardia, Bradycardia, asystole and the like. For example, the arrhythmia detector 134 may also include an on-board R-R interval irregularity (ORI) process 136 that detects the arrhythmia episodes using an automatic detection algorithm that monitors for an irregularity of interest in the ventricular rhythms (e.g., X out of Y beats with no R-wave, X seconds elapsed with no R-wave, etc.). The ORI process 136 may be implemented as firmware, software and/or circuits. For example, the ORI process 136 may implement the AF detection methods described in U.S. Pat. No. 8,135,456, the complete subject matter of which is incorporated herein by reference in its entirety. Optionally, the ORI process 136 may manage a sensitivity profile of the sensor circuit 144 during R-wave detection utilizing an automatic sensing control (ASC) adjustment to determine whether the CA signal has sufficient amplitude to be analyzed for cardiac events. The ORI process 136 identifies R-waves within the CA signals at points where the CA signal crosses the sensitivity profile (outside of a refractory period). The ORI process 136 tracks R-wave and RR intervals within the CA signal and identifies arrhythmia events within the CA signal based on a presence or absence of R-waves and the RR interval. When a sufficient number (e.g., X cardiac events out of Y cardiac events) of the cardiac events within the CA signal are identified as arrhythmia events, the ORI process 136 declares a candidate arrhythmia episode.

The ORI process 136, and other circuits, systems and methods herein, may be implemented in accordance with the embodiments described in pending application Ser. No. 15/973,351, filed May 7, 2018 and titled "Method and System to Detect R-Waves in Cardiac Arrhythmic Patterns", the complete subject matter of which is incorporated herein by reference in its entirety.

The microcontroller 121 also includes a secondary confirmation process 137 configured to be initiated in accordance with one or more of the operations discussed herein. The secondary confirmation process 137 may implement various R-wave detection processes, noise detection processes, P-wave detection processes and the like, as part of the confirmation.

Figure 4B:
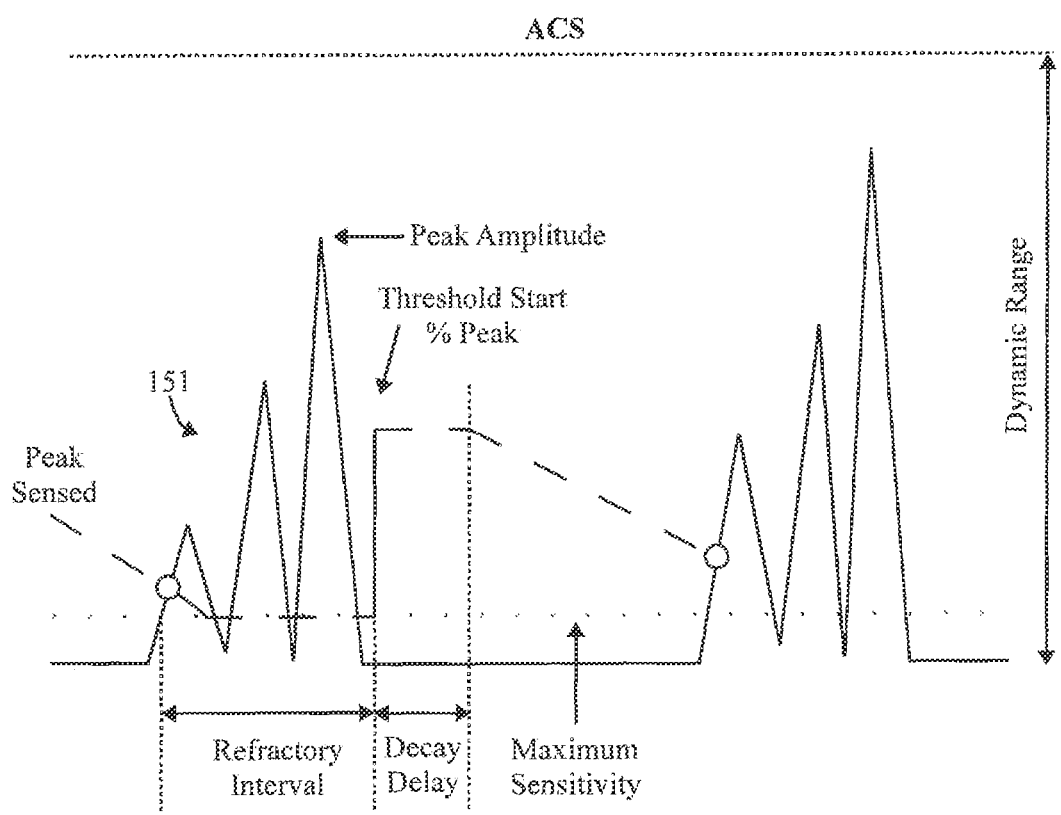
FIG. 4B illustrates an automatic sensing control adjustment utilized by the ORI process of the ICM in accordance with embodiments herein.

FIG. 4B illustrates an automatic sensing control adjustment utilized by the ORI process 136 of the ICM 100 in accordance with embodiments herein. FIG. 4B illustrates an example cardiac activity signal 151 after passing through a rectifier to convert all positive and negative deflections within the cardiac activity signal 151 to be positive deflections. The ORI process 136 manages the sensor circuit 144 to have a sensitivity profile (denoted by a dashed line) that varies over time and is defined by sensitivity profile parameters. The sensitivity profile parameters may be adjusted in accordance with embodiments herein, such as to avoid persistent undersensing.

Returning to FIG. 4A, the ICM 100 further includes an analog-to-digital A/D data acquisition system (DAS) 150 coupled to one or more electrodes via the switch 127 to sample cardiac activity signals across any pair of desired electrodes. The data acquisition system 150 is configured to acquire cardiac electrogram (EGM) signals as CA signals, convert the raw analog data into digital data, and store the digital data as CA data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential arrhythmia episodes.

By way of example, the external device 154 may represent a bedside monitor installed in a patient's home and utilized to communicate with the ICM 100 while the patient is at home, in bed or asleep. The external device 154 may be a programmer used in the clinic to interrogate the ICM 100, retrieve data and program detection criteria and other features. The external device 154 may be a handheld device (e.g., smartphone, tablet device, laptop computer, smartwatch and the like) that can be coupled over a network (e.g., the Internet) to a remote monitoring service, medical network and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, AF detection criteria, activity sensing or other physiological sensors, and electrode polarity, etc.

In addition, the memory 160 stores the cardiac activity data, as well as the markers and other data content associated with detection of arrhythmia episodes. The operating parameters of the ICM 100 may be non-invasively programmed into the memory 160 through a telemetry circuit 164 in telemetric communication via communication link 166 with the external device 154. The telemetry circuit 164 allows intracardiac electrograms and status information relating to the operation of the ICM 100 (as contained in the microcontroller 121 or memory 160) to be sent to the external device 154 through the established communication link 166. In accordance with embodiments herein, the telemetry circuit 164 conveys the cardiac activity data, markers and other information related to episodes.

The ICM 100 may further include magnet detection circuitry (not shown), coupled to the microcontroller 121, to detect when a magnet is placed over the unit. A magnet may be used by a clinician to perform various test functions of the housing 102 and/or to signal the microcontroller 121 that the external device 154 is in place to receive or transmit data to the microcontroller 121 through the telemetry circuits 164.

The ICM 100 can further include one or more physiologic sensors 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 121 for analysis and optional storage in the memory 160 in connection with the cardiac activity data, markers, episode information and the like. While shown as being included within the housing 102, the physiologic sensor(s) 170 may be external to the housing 102, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The battery 172 may afford various periods of longevity (e.g., three years or more of device monitoring). In alternate embodiments, the battery 172 could be rechargeable. See for example, U.S. Pat. No. 7,294,108, Cardiac event micro-recorder and method for implanting same, which is hereby incorporated by reference.

The ICM 100 provides a simple to configure data storage option to enable physicians to prioritize data based on individual patient conditions, to capture significant events and reduce risk that unexpected events are missed. The ICM 100 may be programmable for pre- and post-trigger event storage. For example, the ICM 100 may be automatically activated to store 10-120 seconds of CA data prior to an event of interest and/or to store 10-120 seconds of post CA data. Optionally, the ICM 100 may afford patient triggered activation in which pre-event CA data is stored, as well as post event CA data (e.g., pre-event storage of 1-15 minutes and post-event storage of 1-15 minutes). Optionally, the ICM 100 may afford manual (patient triggered) or automatic activation for CA data. Optionally, the ICM 100 may afford additional programming options (e.g., asystole duration, Bradycardia rate, tachycardia rate, tachycardia cycle count). The amount of CA data storage may vary based upon the size of the memory 160.

The ICM 100 may provide comprehensive safe diagnostic data reports including a summary of heart rate, in order to assist physicians in diagnosis and treatment of patient conditions. By way of example, reports may include episodal diagnostics for auto trigger events, episode duration, episode count, episode date/time stamp and heart rate histograms. The ICM 100 may be configured to be relatively small (e.g., between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

Embodiments may be implemented in connection with one or more implantable medical devices (IMDs). Non-limiting examples of IMDs include one or more of neurostimulator devices, Implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Figure 5:
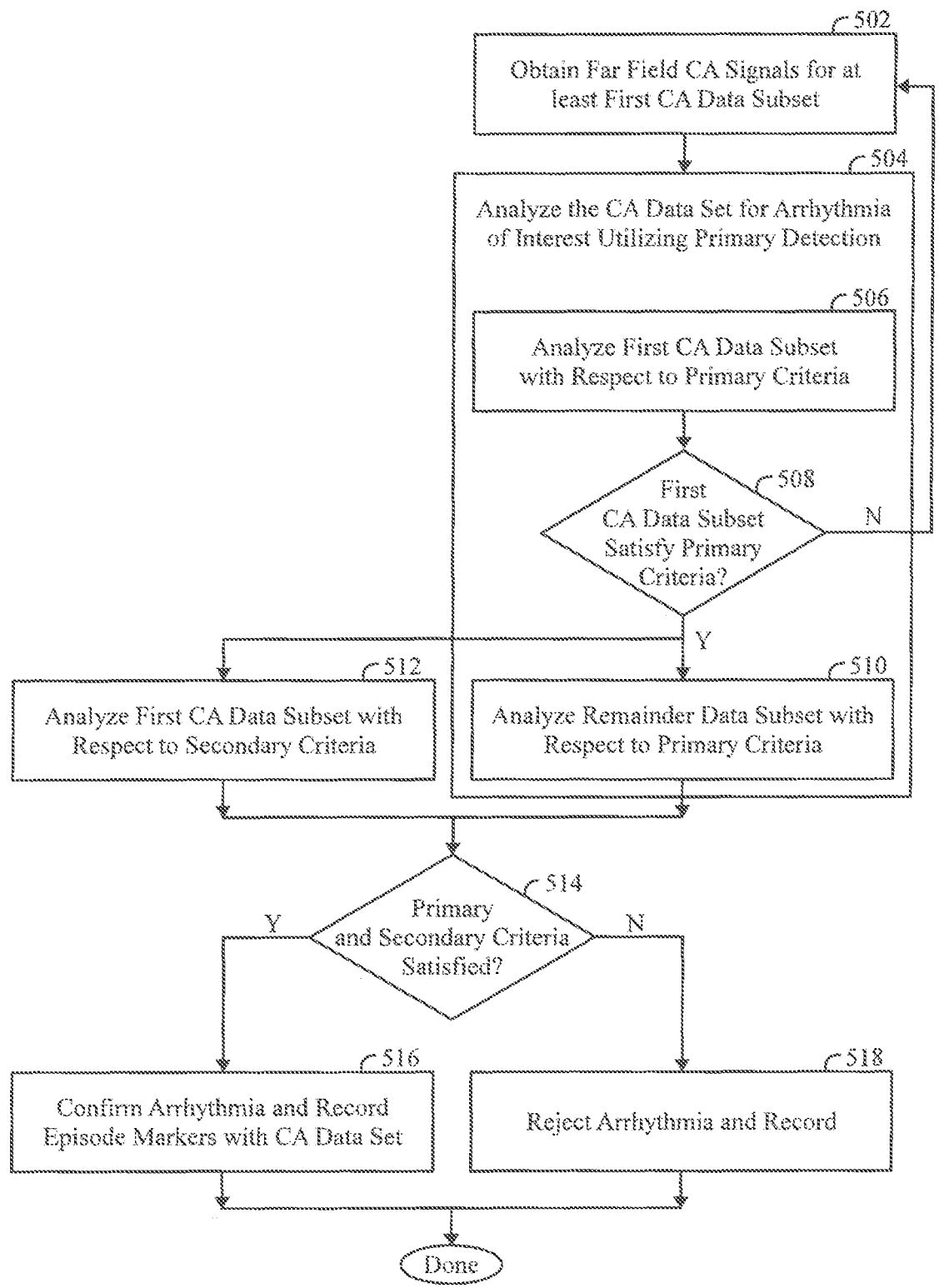
FIG. 5 illustrates a flow chart for a process to accelerate an arrhythmia confirmation of an episode in accordance with embodiments herein.

FIG. 5 illustrates a flow chart for a process to accelerate an arrhythmia confirmation of an episode In accordance with embodiments herein. At 502, one or more processors of the IMD obtain a far field cardiac activity (CA) data set that includes far field CA signals for a series of beats. The CA data set obtained at 502 may be limited to a first CA data subset and/or may also include a remainder CA data subset. Although the operations of FIG. 5 are described in at least a partially serial manner, it is recognized that at least a portion of the operations are performed In parallel. For example, far field CA signals may be obtained continuously through the operations of FIG. 5, while primary detection and/or secondary confirmation processes analyze the incoming CA signals. The far field CA signals are recorded in a circular buffer in a first-in-first-out manner. The buffer is large enough to retain CA signals for a desired number of seconds and/or beats (e.g., 30-60 seconds and/or 15-30 beats). For example, the buffer may be provided with a size sufficient to retain a first CA data subset (e.g., data samples for 28-56 seconds or 12-26 beats) and a remainder CA data subset (e.g., data samples for 2-4 seconds or 3-5 beats).

At 504, the one or more processors analyze the CA data set for an arrhythmia of interest utilizing a primary detection process having primary criteria. The analysis at 504 is divided into first and second phases denoted 506 and 508. At 506, during the initial phase of the primary detection process, the one or more processors analyze the first CA data subset as CA signals are collected to determine whether the first CA data subset satisfies a first portion of the primary criteria.

At 508, the one or more processors determine whether the first CA data subset has satisfied the first portion of the primary criteria. When the first CA data subset does not satisfy the first portion of the primary criteria, flow returns to 502 and new far field CA data signals are obtained. Optionally, counters may be used within the primary criteria, and one or more of the counters may be reset when flow transitions from 508 to 502. For example, if a counter is used to count a number of Bradycardia beats or a time period tracking an asystole window in which no R-waves are detected, the counter may be reset. At 508, when the first CA data subset satisfies the first/initial portion of the primary criteria, the process moves in parallel to 510 and 512.

At 510, the one or more processors analyze the remainder CA data subset to determine whether the remainder CA data subset satisfies a remainder of the primary criteria. At 512, the one or more processors initiate a secondary confirmation process. The operations at 510 and 512 continue in parallel and contemporaneous in time: i) analyzing the first CA data subset utilizing secondary criteria of the secondary confirmation process (at 512) and; ii) analyzing the remainder CA data subset utilizing the primary detection process (at 510). The one or more processors continue the analysis at 510 and 512 until the secondary confirmation process has fully analyzed the first CA data subset at 512 and the primary detection process has fully analyzed the complete CA data set at 510. When the primary detection and secondary confirmation processes are completed at 510 and 512, flow moves to 514.

At 514, the one or more processors determine whether the primary and secondary criteria were satisfied at 510 and 512. When the primary and secondary criteria are satisfied at 510 and 512, flow moves to 516 where the one or more processors confirm a candidate arrhythmia episode that was initially partially indicated at 506.

At 516 or 518, the one or more processors declare the CA data set to exhibit an arrhythmia episode, or reject the candidate arrhythmia episode that was initially partially indicated at 506 when the first CA data subset satisfied the primary arrhythmia criteria. More specifically, at 516, the one or more processors declare the CA data set to exhibit an arrhythmia episode when the first CA data subset satisfies the secondary criteria and the remainder CA data subset satisfies the primary criteria. The one or more processors record an episode marker with the CA data set at a point along the CA signals substantially corresponding to a culmination or conclusion point of the episode designation point, namely a point along the CA signal where the final criteria of the primary criteria occurred. For example, the culmination point may correspond to a peak of an R-wave of a final Bradycardia beat in a series of Y Bradycardia beats. As another example, the culmination point may correspond to an end of an asystole window in which no R-wave was detected.

At 518, the one or more processors declare the CA data set to not exhibit an arrhythmia episode when either or both of i) the first CA data subset does not satisfy the secondary criteria and/or ii) the remainder CA data subset does not satisfy the primary criteria. Additionally or alternatively, at 518, a record may be maintained of rejections of candidate arrhythmias. When a predetermined number candidate arrhythmias are rejected (based on the secondary confirmation process), the one or more processors may inhibit the primary detection process for a predetermined period of time or until parameters are reprogrammed or updated from an external device.

Figure 6:
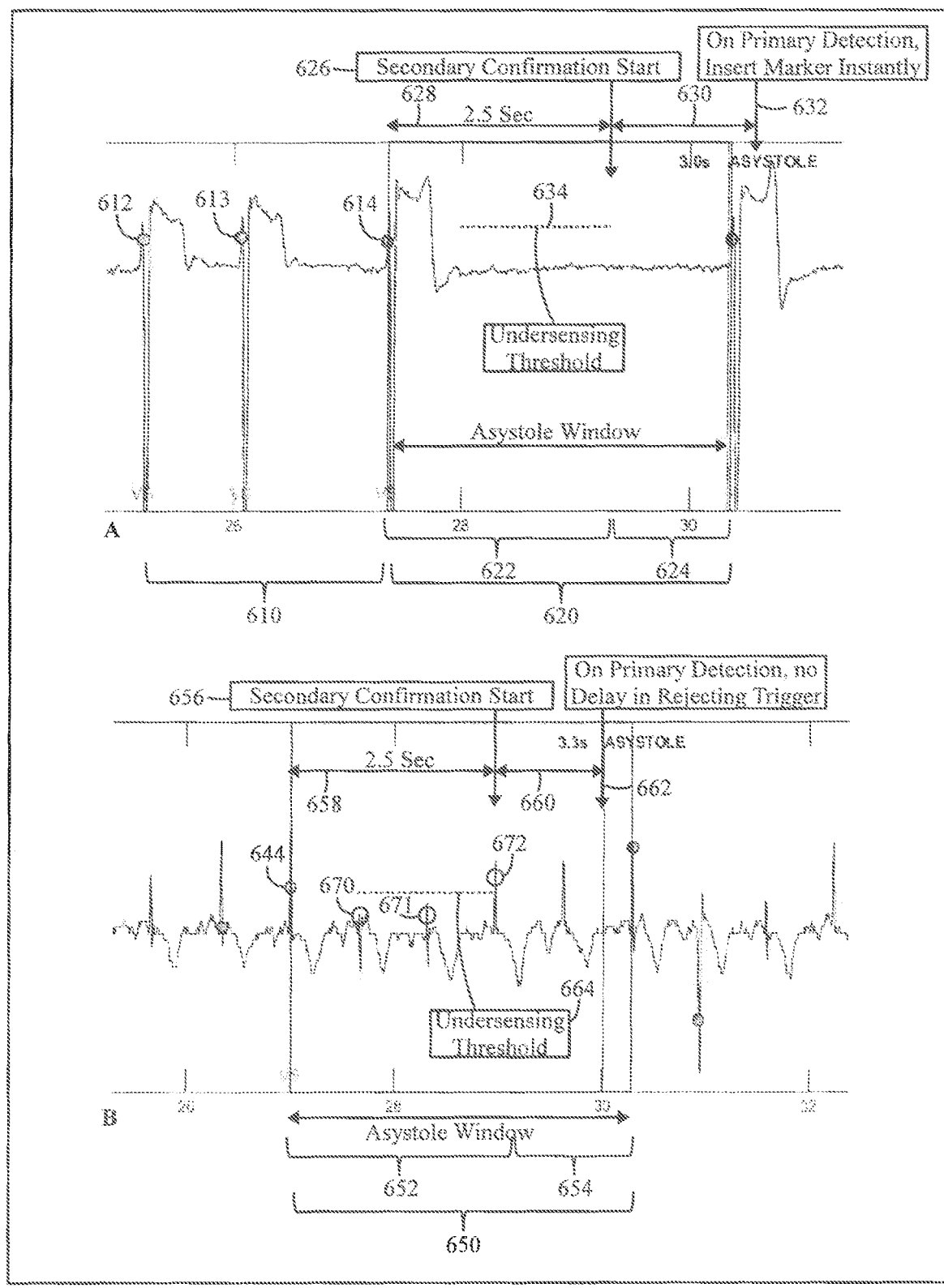
FIG. 6 illustrates timing diagrams for CA signals analyzed by the process of FIG. 5 in connection with detecting and confirming/rejecting an asystole arrhythmia in accordance with embodiments herein.

FIG. 6 illustrates timing diagrams for CA signals analyzed by the process of FIG. 5 in connection with detecting and confirming/rejecting an asystole arrhythmia. Panel A illustrates a CA strip/signal that includes a "true" asystole episode, while Panel B illustrates a CA strip/signal that includes a "false" asystole episode. With reference to Panel A in FIG. 6 and the process of FIG. 5, the CA signal includes a first CA data subset 610 that is analyzed at 506. The primary detection process at 504 searches for R waves within a predetermined period of time, generally referred to as an asystole window. The primary criteria are satisfied when no R-wave is detected during the asystole window. Each time an R-wave is detected, the asystole window/timer is reset. At 504, the first CA data subset 610 is analyzed and R-waves are detected at 612-614, and thus the asystole window/timer never times out. Accordingly, the flow moves through the operations at 502-508, and the decision at 508 determines that successive R waves are detected before expiration of the asystole window. At 508, flow branches to return to 502.

However, following the R-wave 614, the CA signals include a CA data set 620 that undergoes an extended period of time in which no further R waves are detected. The CA data set 620 includes a first CA data subset 622 and a remainder CA data subset 624. During the first CA data subset 622, an asystole timer, associated with the primary criteria, runs for an initial period of time associated with an initial phase 628 (e.g., 2.5 seconds). During the initial phase 628, the first CA data subset 622 is analyzed with respect to the primary criteria to search for an R-wave (e.g., the analysis at 506 in FIG. 5). At 508, the process determines that a portion of the asystole timer for the initial phase 628 has expired/passed without the primary detection process identifying an R-wave.

Accordingly, flow branches from 508 in parallel to 510 and 512. The primary detection process continues (at 510), during a remainder phase 630, by analyzing the remainder CA data subset 624 utilizing the remainder of the primary criteria, namely whether an R-wave is detected during the remainder of the asystole window. The secondary confirmation process is initiated at 512 (FIG. 5) during the remainder phase 630. The duration of the remainder phase 630 may vary, provided that sufficient time is permitted to allow the secondary confirmation process to complete analysis of the first CA data subset. As one example, the remainder phase 630 may be approximately 1 second in length and/or a select number of expected beats. As another example, the remainder phase 630 may generally correspond to the duration of a predetermined number of reference cardiac beats. For example, when a patient exhibits a reference heart rate of 60 beats per minute, then the patient would normally be expected to exhibit 1 intrinsic beat each second. If the secondary confirmation process utilizes up to 1 second of time to analyze a first CA data set, then the remainder phase may be defined to correspond to 1 expected beat.

Panel A also illustrates the point in time, at which the secondary confirmation process is Initiated at 626 with respect to the asystole window. At 512, the secondary confirmation process analyzes the first CA data subset with respect to secondary criteria. The secondary confirmation process may implement various undersensing asystole algorithms, provided that the secondary asystole confirmation process differs from the primary asystole detection process. By way of example, the secondary confirmation process may analyze the first CA data subset 622 to identify an undersensing threshold 634. The secondary confirmation process then compares the first CA data subset 622 to the undersensing threshold 634 to determine whether any R waves are present that were not detected by the primary detection process.

Accordingly, during the remainder phase 630, the first CA data subset 622 is analyzed based on the secondary criteria, while parallel and contemporaneous In time, the remainder CA data subset 624 is analyzed based on the primary criteria. The duration of the initial phase 628 and related portion of the primary criteria may vary. The present example, the initial phase 628 and related portion of the primary criteria may be defined to search for an R-wave for a predetermined number of seconds (e.g., 2.5 seconds). By way of example, the secondary confirmation process that searches for asystole criteria may be initiated a predetermined period of time (e.g., 0.5 seconds) before the asystole timer of the primary asystole detection process expires. The secondary confirmation process uses the first CA data subset which represents all of the CA data available up to the point In time when the secondary confirmation process is initiated. The secondary confirmation process evaluates the first CA data subset to determine whether to confirm or reject a candidate asystole episode that may be declared by the primary detection process at the end of the asystole window. Regardless of the culmination or cut-off point in time for the end of the asystole window, the result of the secondary confirmation process will not take effect until the primary detection process declares a candidate asystole episode as noted at 632 in panel A of FIG. 6.

Additionally or alternatively, the secondary confirmation process may store the undersensing threshold 634 (dotted line in panel A) determined from the analysis of the first CA data subset 622 and apply the same under-sensing threshold 634 to test the remainder CA data subset 624 when the primary detection process triggers asystole with negligible processing time. Additionally or alternatively, the secondary confirmation process may be split to compute the under-sensing threshold based on the first CA data subset and subsequently, when the primary detection process declares a candidate asystole episode, the secondary confirmation process may then utilize the undersensing threshold to test the complete CA data set within the asystole window to save processing cycles in the case of false pre-triggers at 626.

In the example of panel A in FIG. 6, the primary detection and secondary confirmation processes both confirm an asystole episode. Accordingly, an asystole marker is inserted at 632 immediately after completion of the primary detection process. No delay is experienced following detection of the culmination point in the CA data set (e.g., completion of the primary detection process) before the asystole marker is inserted.

An alternative example is illustrated at panel B in FIG. 6, namely a situation in which the primary detection process falsely declares a positive asystole episode. Following an R-wave 644, the CA signals include a CA data set 650 that undergoes an extended period of time in which no further R waves are detected. The CA data set 650 includes a first CA data subset 652 and a remainder CA data subset 654. During the first CA data subset 652, the asystole timer, associated with the primary criteria, runs for an initial period of time associated with an initial phase 658 (e.g., 2.5 seconds). During the initial phase 658, the first CA data subset 652 is analyzed with respect to the primary criteria (e.g., the analysis at 506 in FIG. 5), and the process determines that the asystole window/timer for the initial phase 652 has expired before the primary detection process identified in R-wave. Accordingly, flow branches from 508 in parallel to 510 and 512. The primary detection process continues (at 510), during a remainder phase 660 of the primary detection process, by analyzing the remainder CA data subset 654 utilizing the primary criteria, namely whether an R-wave is detected during the asystole window. The secondary confirmation process is initiated during the remainder phase 660. Panel B also illustrates the point in time, within the asystole window, at which the secondary confirmation process is initiated at 656. At 512, the secondary confirmation process analyzes the first CA data subset with respect to secondary criteria.

During the remainder phase 660, the first CA data subset 652 is analyzed based on the secondary criteria, while parallel and contemporaneous in time, the remainder CA data subset 654 is analyzed based on the primary criteria. The secondary confirmation process uses the first CA data subset which represents all of the CA data available up to the point in time when the secondary confirmation process is initiated. The secondary confirmation process evaluates the first CA data subset to determine and under-sensing threshold 664 and then analyzes the first CA data subset with respect to the under-sensing threshold 664. In the example of panel B, the secondary confirmation process determines that R waves were under sensed by the primary detection process. For example, the secondary confirmation process may identify under sensed R waves at 670-672. The primary detection process ends at 662 and falsely declares a positive candidate asystole episode. However, the secondary confirmation process rejects the candidate asystole episode due to under-sensing.

Optionally, the process described in connection with FIG. 6 may be modified to initiate the secondary confirmation process when a smaller portion or set of the primary criteria are satisfied. For example, when the primary detection process utilizes an asystole window of Y seconds to declare an asystole episode, the secondary confirmation process may be initiated when only one second, two seconds, Y−2 seconds, Y−3 seconds, etc., of beats are identified with no R waves. In this alternative example, the secondary confirmation process may be initiated sooner, than in the foregoing examples, because under-sensing normally will be manifest equally during earlier and later parts of an asystole arrhythmia. Accordingly, only a beginning portion of the CA data set needs to be checked.

Figure 7:
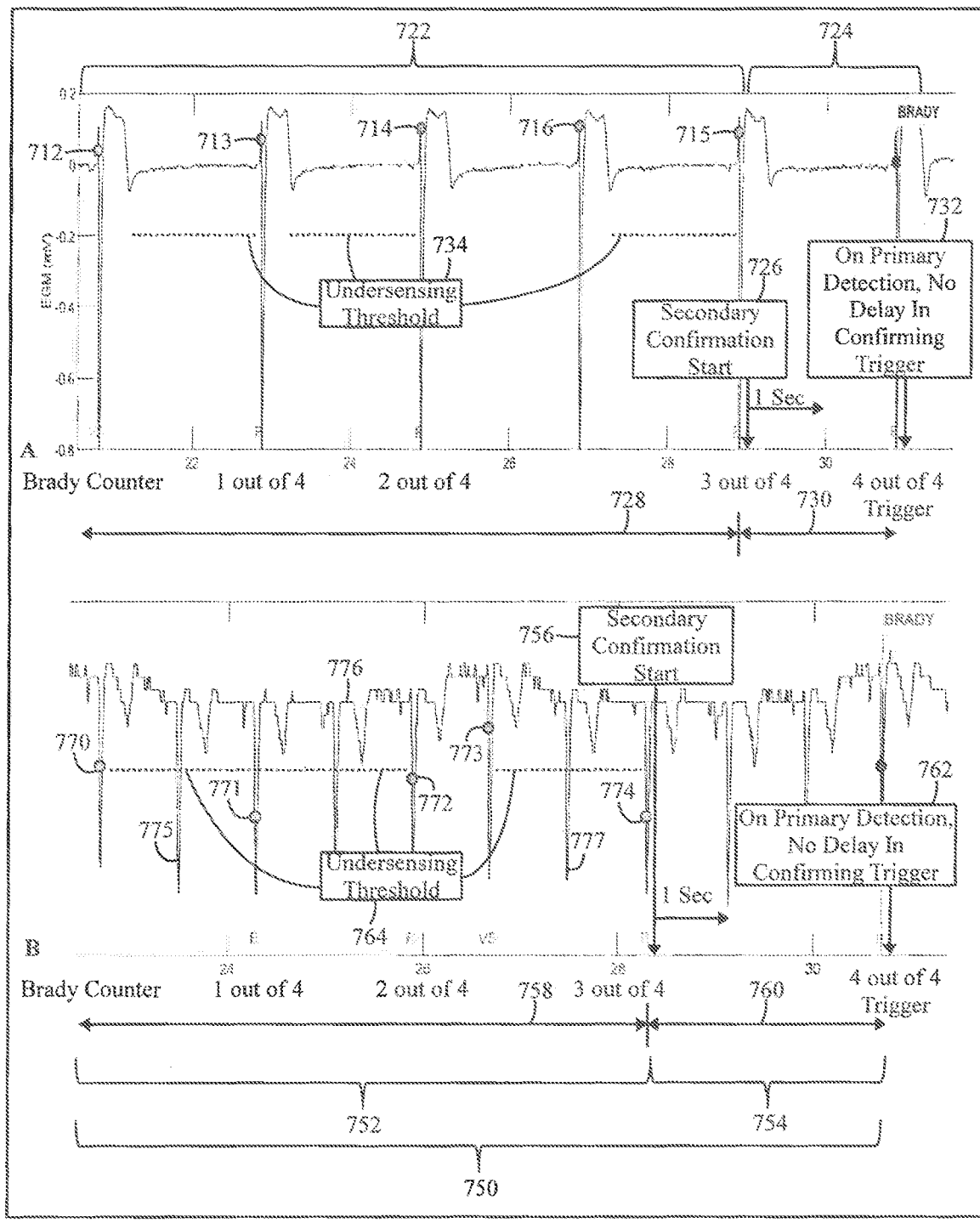
FIG. 7 illustrates timing diagrams for CA signals analyzed by the confirmation management process of FIG. 5 in connection with detecting a Bradycardia arrhythmia in accordance with embodiments herein.

FIG. 7 illustrates timing diagrams for CA signals analyzed by the confirmation management process of FIG. 5 in connection with detecting a Bradycardia arrhythmia. Panel A illustrates a CA signal that includes a "true" Bradycardia episode, while Panel B illustrates a CA signal that includes a "false" Bradycardia episode. With reference to Panel A in FIG. 7 and the process of FIG. 5, the CA signal includes a first CA data subset 722 that is obtained and analyzed at 506. The primary detection process at 504 utilizes a primary criteria that searches for R waves, determines whether an R-R interval exceeds a predetermined RR interval Brady threshold, and determines whether a predetermined number of successive beats have RR intervals that exceed the RR interval Brady threshold.

With reference to panel A of FIG. 7, the primary detection process identifies R waves at 712-715. The process labels the beats at 713-715 to represent Brady beats as denoted by the "B". The process does not identify the R-wave at 716 and thus treats the interval between R waves at 714 and 715 to represent one RR interval. The first CA data subset 722 includes three Brady beats (at 713-715), thereby satisfying the portion of the primary criteria associated with an initial phase 728 of the primary detection process. In the present example, the portion of the primary criteria represent a determination of three consecutive Brady beats or Y−1 successive Brady beats out of Y successive Brady beats. Optionally, the portion of the primary criteria to be applied to the first CA data subset 722 may differ, such as a different number of consecutive Brady beats, a number of Brady beats Y−1 out of a number of beats Y, or a number of Brady beats X out of a number of beats Y otherwise.

At 508, the process determines that the Brady counter for the initial phase 728 has reached the predetermined count (e.g., Y−1) of the primary detection process. Accordingly, flow branches from 508 in parallel to 510 and 512. The primary detection process continues (at 510), during a remainder phase 730 of the primary detection process, by analyzing the remainder CA data subset 724 utilizing the remaining portion of the primary criteria, namely whether a predetermined number of additional successive beats are separated by an RR interval Brady threshold, thereby designating the successive beats as Brady beats. The secondary confirmation process is initiated at 512 (FIG. 5) during the remainder phase 730. Panel A also illustrates the point In time, within the Brady window, at which the secondary confirmation process is initiated at 726. At 512, the secondary confirmation process analyzes the first CA data subset 722 with respect to secondary criteria. The secondary confirmation process may implement various undersensing algorithms, provided that the secondary confirmation process differs from the primary Bradycardia detection process. By way of example, the secondary confirmation process may analyze the first CA data subset to identify an under-sensing threshold 734. The secondary confirmation process then compares the first CA data subset 722 to the under-sensing threshold 734 to determine whether any R waves are present that were not detected by the primary detection process.

Accordingly, during the remainder phase 730, the first CA data subset 722 is analyzed based on the secondary criteria, while parallel and contemporaneous in time, the remainder CA data subset 724 is analyzed based on the primary criteria. The duration of the initial phase 728 and related portion of the primary criteria may vary.

Regardless of the number of Brady beats utilized for the primary criteria, the result of the secondary confirmation process will not take effect until the primary detection process declares a candidate Bradycardia episode as noted at 732 in panel A of FIG. 7. By way of example, the secondary confirmation process is executed after Y−1 out of Y Bradycardia beats have been detected consecutively. The secondary confirmation process is able to analyze all of the data in the first CA data subset 722 and evaluate whether one or more of the Brady beats declared by the primary detection process are confirmed or rejected. The secondary confirmation process is able to complete the analysis, for example within one second, and provide an outcome indicating whether to confirm or reject a Brady episode, such that the results of the secondary confirmation process are ready before or substantially the same time as the completion of the primary detection process.

An alternative example is illustrated at panel B in FIG. 7, namely a situation in which the primary detection process falsely declares a positive Bradycardia episode. A CA data set 750 is illustrated that includes a first CA data subset 752 and a remainder CA data subset 754. During the initial phase 758, the first CA data subset 752 is analyzed and the primary detection process detects R waves at 770-774. The primary detection process labels the beats at 771, 772 and 774 to represent Brady beats, thereby satisfying the initial portion of the primary criteria, namely Y−1 Brady beats. Accordingly, flow branches from 508 in parallel to 510 and 512. The primary detection process continues (at 510), during a remainder phase 760 of the primary detection process, by analyzing the remainder CA data subset 754 utilizing the primary criteria, namely whether one (or a predetermined number) of additional successive beats are declared Brady beats. The secondary confirmation process is initiated during the remainder phase 760. Panel B also illustrates the point in time, within the Brady count, at which the secondary confirmation process is initiated at 756. At 512, the secondary confirmation process analyzes the first CA data subset with respect to secondary criteria.

During the remainder phase 760, the first CA data subset 752 is analyzed based on the secondary criteria, while parallel and contemporaneous in time, the remainder CA data subset 754 is analyzed based on the primary criteria. The secondary confirmation process uses the first CA data subset which represents all of the CA data available up to the point in time when the secondary confirmation process is initiated. The secondary confirmation process evaluates the first CA data subset to determine an under-sensing threshold 764 and then analyzes the first CA data subset with respect to the under-sensing threshold 764. In the example of panel B, the secondary confirmation process determines that R waves were under sensed by the primary detection process. For example, the secondary confirmation process may identify under-sensed R waves at 775-777. The primary detection process ends at 762 and falsely declares a positive candidate Bradycardia episode. However, the secondary confirmation process rejects the candidate Bradycardia episode due to under-sensing of the R waves 775-777.

Additionally or alternatively, when the secondary confirmation process rejects the Brady episode, the Brady counters may be reset preempting further analysis by the primary detection process during the remainder phase 760.

Optionally, the process described in connection with FIG. 7 may be modified to initiate the secondary confirmation process when a smaller set of the primary criteria are satisfied. For example, when the primary detection process utilizes primary criteria of Y Bradycardia beats to declare a Bradycardia episode, the secondary confirmation process may be initiated when only one, two, Y-2, Y-3, etc., Bradycardia beats are identified. In this alternative example, the secondary confirmation process may be initiated sooner, than in the foregoing examples, because under-sensing normally will be manifest equally during earlier and later parts of a Bradycardia arrhythmia. Accordingly, only a beginning portion of the CA data set needs to be checked.

Figure 8:
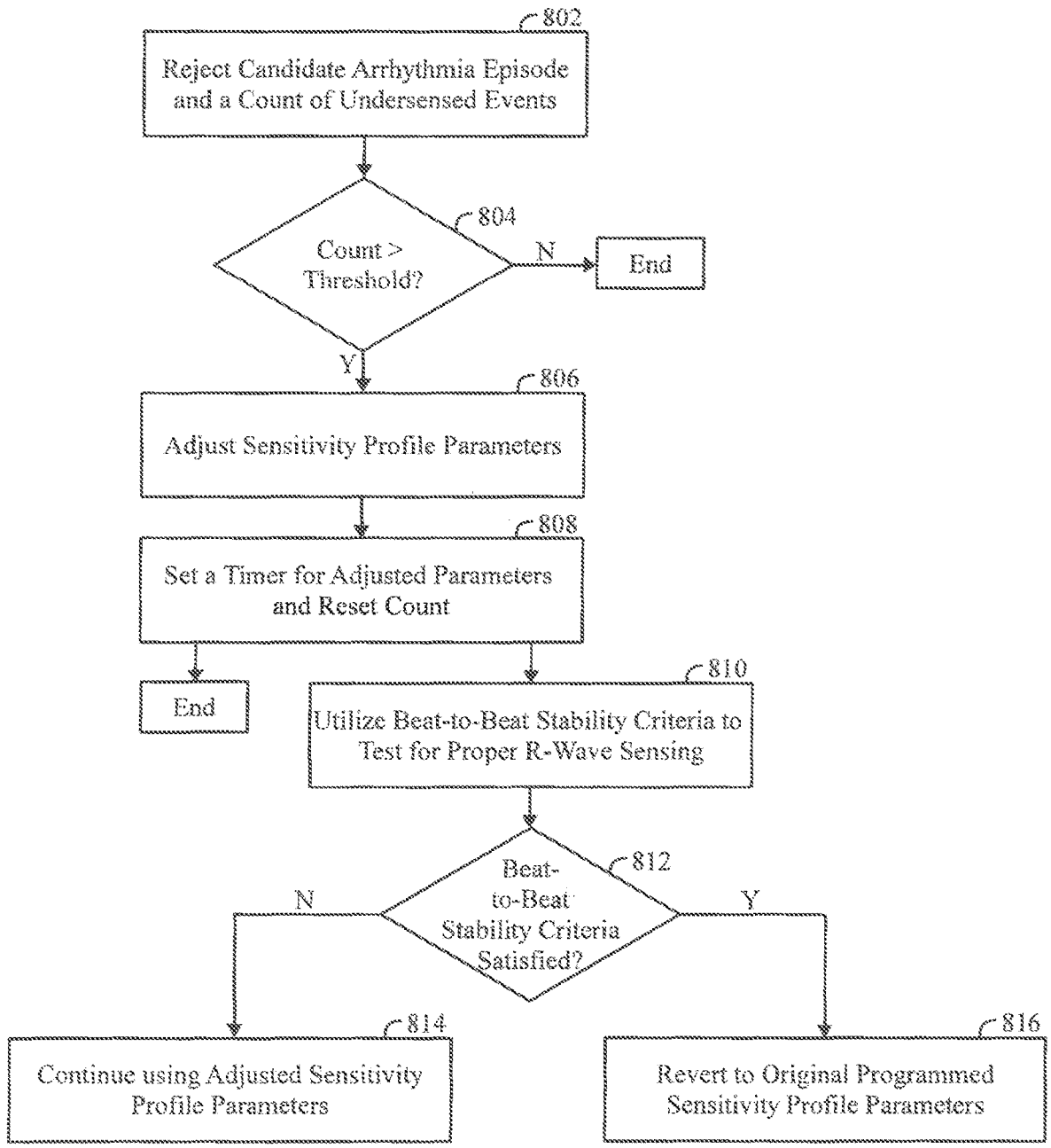
FIG. 8 illustrates a flowchart for process utilized for dynamically lowering a sensitivity threshold utilized by the primary detection process In the presence of persistent under-sensing in accordance with embodiments herein.

FIG. 8 illustrates a flowchart for process utilized for dynamically lowering a sensitivity threshold utilized by the primary detection process in the presence of persistent under-sensing in accordance with embodiments herein. The operations of FIG. 8 are implemented in connection with the operations of FIG. 5 (e.g., following the arrhythmia rejection at 518). At 802, the one or more processors reject a candidate arrhythmia episode and update a count of under sensed events. The count may be incremented by one each iteration through the operations of FIG. 8. Alternatively, the count may be incremented for each individual R wave that was under sensed during the current analysis of the first CA data subset by the secondary confirmation process.

At 804, the one or more processors determine whether the count of under sensed events has exceeded a threshold (e.g., 20-30 under sensed events). When the count of under sensed events does not exceed the threshold, the process ends until the next arrhythmia. Alternatively, when the count of under sensed events does exceed the threshold, flow continues to 806. Persistent under-sensing may occur due to an R wave amplitude drop off (in the sensed CA signals) below the program to maximum sensitivity or due to another sensitivity profile parameter. Accordingly, at 806, the one or more processors adjust one or more sensitivity profile parameters, such as to lower the programmed maximum sensitivity by a predetermined increment. The adjusted sensitivity profile parameters (e.g., reduced programmed maximum sensitivity) is then utilized by the primary detection process.

As one nonlimiting example, after the secondary detection process rejects 4 false candidate Bradycardia episodes within a 1 minute period of time, the programmed maximum sensitivity may be iteratively reduced by 0.025 mV increments (capped to 0.075 mV) to mitigate undersensing.

At 808, the one or more processors set a timer that defines a time duration for which the primary detection process will utilize the adjusted sensitivity profile parameters (e.g., reduced programmed maximum sensitivity). At 808, the one or more processors also reset the counter that counts rejected candidate arrhythmia episodes. Thereafter, the process of FIG. 8 may pursue 2 alternative paths. Along one path/option, the process of FIG. 8 ends.

The primary detection process utilizes the adjusted sensitivity profile parameters (e.g., reduced programmed maximum sensitivity) until the timer (set at 808) times out, after which the primary detection process reverts/returns to the original sensitivity profile parameters (e.g., programmed maximum sensitivity). Additionally or alternatively, before reverting to the original sensitivity profile parameters (e.g., programmed maximum sensitivity) post persistent under-sensing, the secondary confirmation process may be evaluated to verify that undersensing is not occurring. By utilizing the secondary confirmation process in this manner, embodiments herein lead to processing time saving and avoiding false detections.

Additionally or alternatively, the process of FIG. 5 may continue to be implemented, even while the primary detection process utilizes the adjusted sensitivity profile parameters. In the event that the primary detection process continues to under sensed events, the process of FIG. 8 may be repeated. For example, when the count of rejected candidate arrhythmia episodes again exceeds the threshold, flow may continue from 802 to 806, where the programmed maximum sensitivity is again reduced by an additional amount. The timer may be reset at 808 to allow the primary detection process to utilize the newly reduced maximum sensitivity for the predetermined time duration. The operations of FIG. 8 may continue to repeat until the program maximum sensitivity is sufficiently reduced such that the primary detection process no longer experiences persistent under-sensing.

Figure 9:
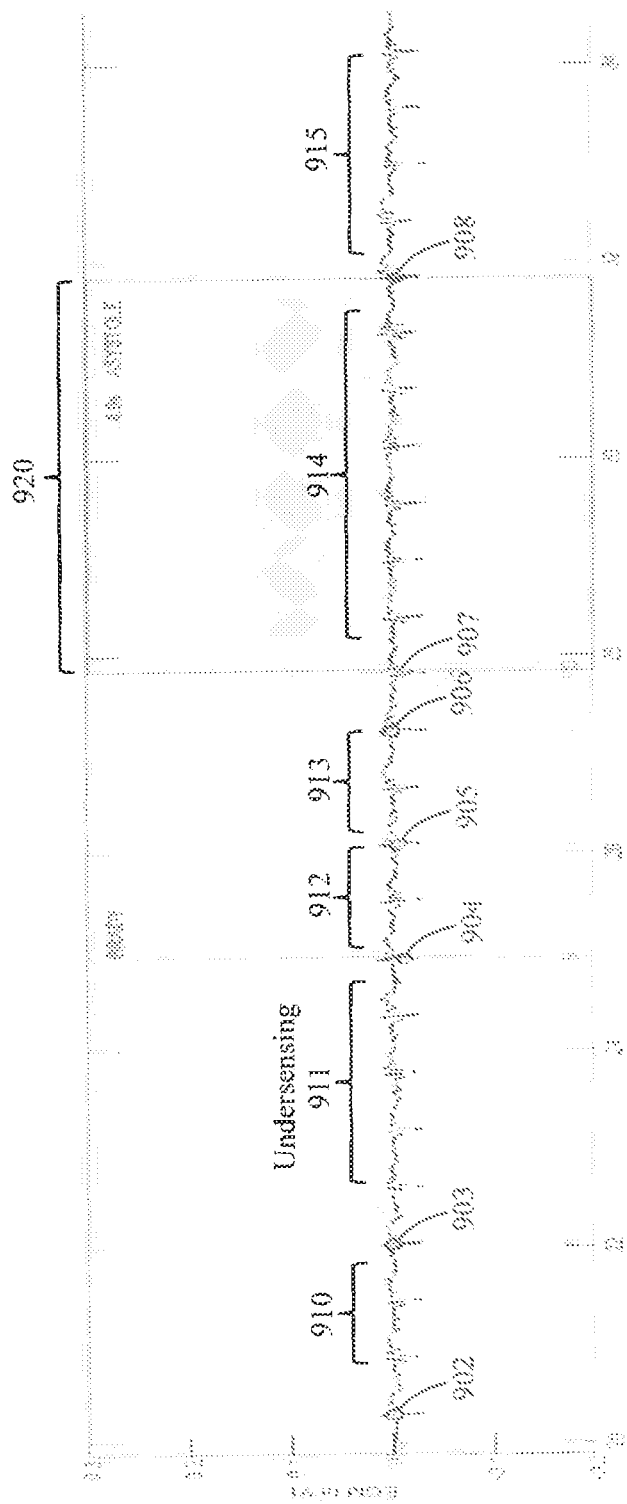
FIG. 9 illustrates a timing diagram of CA signals, for which the primary detection process may experience persistent under-sensing in accordance with embodiments herein.

FIG. 9 illustrates a timing diagram of CA signals, for which the primary detection process may experience persistent under-sensing. The timing diagram of FIG. 9 illustrates R waves that are detected by the primary detection process at 902-908. The primary detection process under senses R waves In the beats noted at 910-915. Due to the under-sensing, Bradycardia beats are declared at 903 and 904, while an asystole interval is declared at 920. The secondary confirmation process would identify the under sensed R waves in the beats 910-915 and reject any Bradycardia or asystole arrhythmia declared by the primary detection process. In the event that the conditions illustrated in FIG. 9 persist, the process of FIG. 8 would increment the count of rejected candidate arrhythmia episodes until reaching the count threshold. The process of FIG. 8 would then lower the programmed maximum sensitivity utilized by the primary detection process as described herein. By lowering the programmed maximum sensitivity of the primary detection process, the secondary confirmation processing and primary detection processing is reduced thereby leading to a reduced duty cycle and more accurate assignment of event/beat markers.

Returning to 808, an alternative path may be followed once the sensitivity profile parameter(s) are adjusted, the timer is set and the candidate arrhythmia episode counter is reset, namely flow may move to 810.

At 810, the one or more processors utilize a beat to beat stability criteria to test for proper R wave sensing. Various criteria may be utilized while the adjusted sensitivity profile parameters are used. For example, beat-to-beat variability metrics may include one or more of an RR interval, R wave amplitude, R wave "area under the curve" and the like. At 810, the one or more processors calculate one or more of the variability metrics for a series of beats of interest (e.g., seven beats). For example, a variability between RR intervals over a series of beats may be determined and compared to a variability threshold. By way of example, the processors may determine the stability of the RR interval for a previous series of beats (the previous 7 RR interval), such as to determine an $RR\_metric=|RR_7-\frac{1}{6}*\Sigma RR_i|$, $i=1:6$ (metric of RR interval variability). When the $RR\_metric<\Delta RR\_threshold$, this may be determined as an indication to keep the lowered maximum sensitivity.

Additionally or alternatively, a variability in R wave amplitude and/or a variability of the R wave "area under the curve" may be determined and compared to corresponding variability thresholds. As another example, the processors may determine the stability of R peak amplitude, such as to determine R-peak_metric=|R-peak$_7$−⅙*ΣR-Peak$_i$|i=1:6 (metric of R-Peak variability). When the R-peak_metric<R-peak_threshold, this may be determined as an indication to keep the lowered maximum sensitivity. As another example, the processors may determine the stability of QRS-wave energy, such as to determine QRS-AUC_metric=|QRS-AUC$_i$−⅙*ΣQRS-AUC$_i$| i=1:6, (metric of QRS-wave area-under-curve variability). When the QRS-AUC_metric<QRS-AUC_threshold, this may be determined it is an indication to keep the lowered maximum sensitivity.

At 812, the one or more processors determine whether one or more of the variability metrics satisfy the corresponding variability threshold. When some or all of the variability metrics do not satisfy the corresponding thresholds, flow moves to 816. Otherwise, when the variability metrics are below the corresponding variability thresholds, flow moves to 814. At 814, the one or more processors continue to use the adjusted sensitivity profile parameters (as set at 808). At 816, the one or more processors revert to the original sensitivity profile parameters. The operations at 810-816 may be implemented in real time with a minimal processing overhead.

The operations at 810-816 incrementally lower a maximum sensitivity, and if there is still variability (indicated by some or all of the variability metric criteria not met), it could indicate T-wave/P-wave/noise over-sensing or irregular heart rate. Accordingly, it may be desirable to revert to the original sensitivity profile parameters. Reverting to the original sensitivity profile parameters allows primary sensing to evaluate the rhythm and run secondary confirmation as needed.

Figure 10:
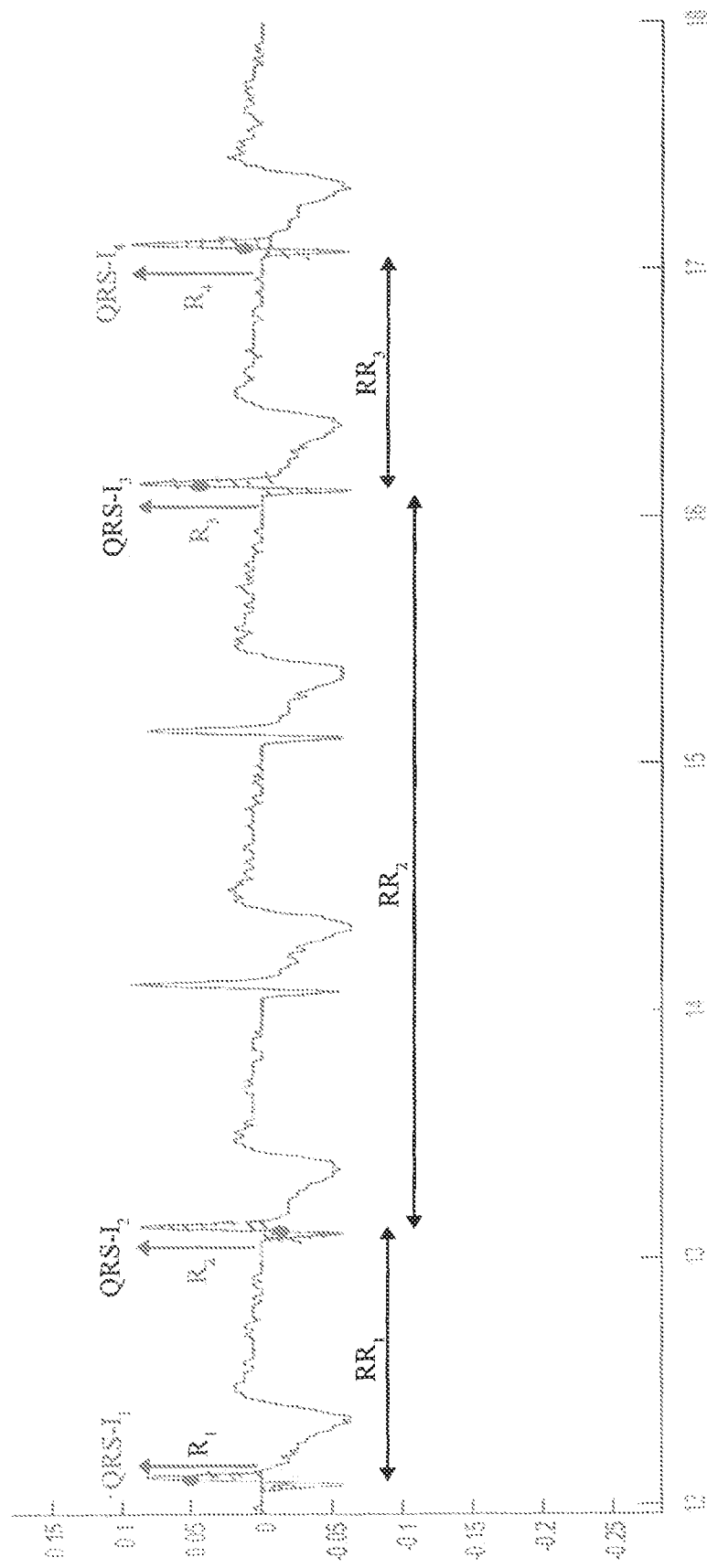
FIG. 10 illustrates a CA signal trace that may be analyzed in connection with the process of FIG. 8 in accordance with embodiments herein.

FIG. 10 illustrates an CA signal trace that may be analyzed in connection with the process of FIG. 8 in accordance with embodiments herein. With reference to the operations of FIG. 8, at 810, the one or more processors may analyze the RR intervals, denoted as RR1, RR2, RR3 and to determine variability there between. Additionally or alternatively, the processors may analyze the R wave amplitudes, as noted at R1, R2, R3, R4 in FIG. 10 and determine variability there between. Additionally or alternatively, the processors may analyze the R wave area under the curves as denoted at QRS-11, QRS-12, QRS-13, and QRS-14 and determine variability there between. At 812, the one or more processors compare the level of variability to one or more thresholds to determine whether the CA signal trace exhibits a stable or instable beat-to-beat pattern, and based thereon performs the operations described in connection with FIG. 8.

In a Bradycardia training dataset of 1811 Bradycardia events, embodiments herein afforded a mechanism to enable markers to be generated and recorded with real time EGM signals with no delay.

In accordance with embodiments herein, the secondary confirmation process is estimated to take approximately 0.5 second to analyze a corresponding CA data subset. By way of example, primary Brady detection processes may experience under-sensing in the order of 10's-100's of events per day leading to additional battery consumption. Dynamically lowering maximum sensitivity when persistent undersensing is detected can dramatically reduce the number of these evaluations by an estimated 70% thus reducing the impact on battery longevity by days to weeks.

In an asystole training dataset of 2180 asystole events, Embodiments herein afforded a mechanism to enable markers to be generated and recorded with real time EGM signals with no delay following an episode declaration point along the EGM strip (e.g., marker delay was 0 secs). A secondary confirmation process in accordance with embodiments herein is estimated to take approximately 0.5 seconds to analyze a corresponding CA data subset. By way of example, the primary asystole detection process may experience under-sensing in the order of 10's-100's events per day. Lowering maximum sensitivity when persistent under-sensing is detected by discrimination can dramatically reduce the number of these evaluations by an estimated 70% thus dramatically reducing the impact on battery longevity by days to weeks.

CLOSING

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A system for accelerating confirmation of cardiac arrhythmias, comprising:
   memory to store specific executable instructions;
   one or more processors configured to execute the specific executable instructions for:
      obtaining a far field cardiac activity (CA) data set that includes far field CA signals for a series of beats, the CA data set including a first CA data subset and a remainder CA data subset;
      analyzing the CA data set for an arrhythmia of interest utilizing a primary detection process having primary criteria;
      during a first phase of the primary detection process, analyzing the first CA data subset to determine whether the first CA data subset satisfies at least a portion of the primary criteria;
      when the first CA data subset satisfies at least the portion of the primary criteria, initiating a secondary confirmation process;
      parallel and contemporaneous in time:
         i) analyzing the first CA data subset utilizing secondary criteria associated with the secondary confirmation process and;
         ii) analyzing the remainder CA data subset utilizing the primary criteria;
      declaring the CA data set to exhibit an arrhythmia episode when the first CA data subset satisfies the secondary criteria and the remainder CA data subset satisfies a remainder of the primary criteria.

2. The system of claim 1, wherein the one or more processors are configured to complete the i) analysis of the first CA data set by the secondary confirmation process before or substantially contemporaneous in time with completion of the analysis of the remainder of the CA data subset by the primary detection process.

3. The system of claim 1, wherein the one or more processors are further configured to reject the arrhythmia episode when at least one of the i) analysis determines that the first CA data subset does not satisfy the secondary criteria or the ii) analysis determines that the remainder CA data subset does not satisfy the primary criteria.

4. The system of claim 1, wherein the primary detection process detects Bradycardia episodes, the one or more processors configured to initiate the secondary confirmation process in response to the first CA data subset including a first number of Bradycardia beats, the one or more processors configured to implement the ii) analysis by determining that the remainder CA data subset satisfies the remainder of the primary criteria when the remainder CA data subset includes a second number of Bradycardia beats.

5. The system of claim 1, wherein the at least the portion of the primary criteria include an initial criteria to be applied to the first CA data subset and a remainder of the primary criteria to be applied to the remainder CA data subset.

6. The system of claim 1, wherein the primary detection process detects asystole episodes, the one or more processors configured to initiate the secondary confirmation process in response to the first CA data subset including a first time interval during which no R waves are detected by the primary detection process, the one or more processors configured to declare a candidate asystole episode when the ii) analysis determines that the primary detection process does not detect an R-wave during the remainder CA data subset.

7. The system of claim 1, wherein the primary detection process detects Bradycardia episodes, the one or more processors configured to initiate the secondary confirmation process in response to the primary detection process determining that the first CA data subset exhibits a number of Bradycardia events, the one or more processors configured to declare a candidate Bradycardia episode when the ii) analysis determines that the primary detection process detects at least one Bradycardia event during the remainder CA data subset.

8. The system of claim 1, wherein the one or more processors are further configured to record a Brady or asystole marker with the CA data set at a point along the CA data set that substantially corresponds in time to a culmination point along the CA dataset of a corresponding Brady or asystole episode.

9. The system of claim 1, wherein the one or more processors are further configured to maintain a count of candidate arrhythmia episodes that are rejected based on the secondary confirmation process; and to adjust a sensitivity profile parameter of the primary detection process based on the count.

10. The system of claim 9, wherein the one or more processors are further configured to revert to a programmed sensitivity profile of the primary detection process after expiration of a timer.

11. A computer implemented method for accelerating confirmation of cardiac arrhythmias, the method comprising:
   under control of one or more processors configured with specific executable instructions,
      obtaining a far field cardiac activity (CA) data set that includes far field CA signals for a series of beats, the CA data set including a first CA data subset and a remainder CA data subset;
      analyzing the CA data set for an arrhythmia of interest utilizing a primary detection process having primary criteria;

during a first phase of the primary detection process, analyzing the first CA data subset to determine whether the first CA data subset satisfies at least a portion of the primary criteria;

when the first CA data subset satisfies at least the portion of the primary criteria, initiating a secondary confirmation process;

parallel and contemporaneous in time:
  i) analyzing the first CA data subset utilizing secondary criteria associated with the secondary confirmation process and;
  ii) analyzing the remainder CA data subset utilizing the primary criteria;

declaring the CA data set to exhibit an arrhythmia episode when the first CA data subset satisfies the secondary criteria and the remainder CA data subset satisfies a remainder of the primary criteria.

12. The method of claim 11, further comprising completing the i) analysis of the first CA data set by the secondary confirmation process before or substantially contemporaneous in time with completion of the analysis of the remainder of the CA data subset by the primary detection process.

13. The method of claim 11, further comprising rejecting the arrhythmia episode when at least one of the i) analysis determines that the first CA data subset does not satisfy the secondary criteria or the ii) analysis determines that the remainder CA data subset does not satisfy the primary criteria.

14. The method of claim 11, wherein the primary detection process detects Bradycardia episodes, the method initiating the secondary confirmation process in response to the first CA data subset including a first number of Bradycardia beats, the method implementing the ii) analysis by determining that the remainder CA data subset satisfies the remainder of the primary criteria when the remainder CA data subset includes a second number of Bradycardia beats.

15. The method of claim 11, wherein the at least the portion of the primary criteria include an initial criteria to be applied to the first CA data subset and a remainder of the primary criteria to be applied to the remainder CA data subset.

16. The method of claim 11, wherein the primary detection process detects asystole episodes, the method initiating the secondary confirmation process in response to the first CA data subset including a first time interval during which no R waves are detected by the primary detection process, the method declaring a candidate asystole episode when the ii) analysis determines that the primary detection process does not detect an R-wave during the remainder CA data subset.

17. The method of claim 11, wherein the primary detection process detects Bradycardia episodes, the method initiating the secondary confirmation process in response to the primary detection process determining that the first CA data subset exhibits a select number of Bradycardia events, the method declaring a candidate Bradycardia episode when the ii) analysis determines that the primary detection process detects at least one Bradycardia event during the remainder CA data subset.

18. The method of claim 11, further comprising recording a Brady or asystole marker with the CA data set at a point along the CA data set that substantially corresponds in time to a culmination point of a corresponding Brady or asystole episode.

19. The method of claim 11, further comprising maintaining a count of candidate arrhythmia episodes that are rejected based on the secondary confirmation process; and adjusting a sensitivity profile parameter based on the count.

20. The method of claim 19, further comprising utilizing a beat to beat stability criteria to test for proper R wave sensing, and based thereon adjusting a sensitivity profile parameter, the beat-to-beat variability metrics including one or more of an RR interval, R wave amplitude, or R wave area-under-the-curve.

* * * * *